Oct. 1, 1974 R. L. BYRUM Plant Pat. 3,631
ROSE PLANT
Filed Nov. 7, 1973
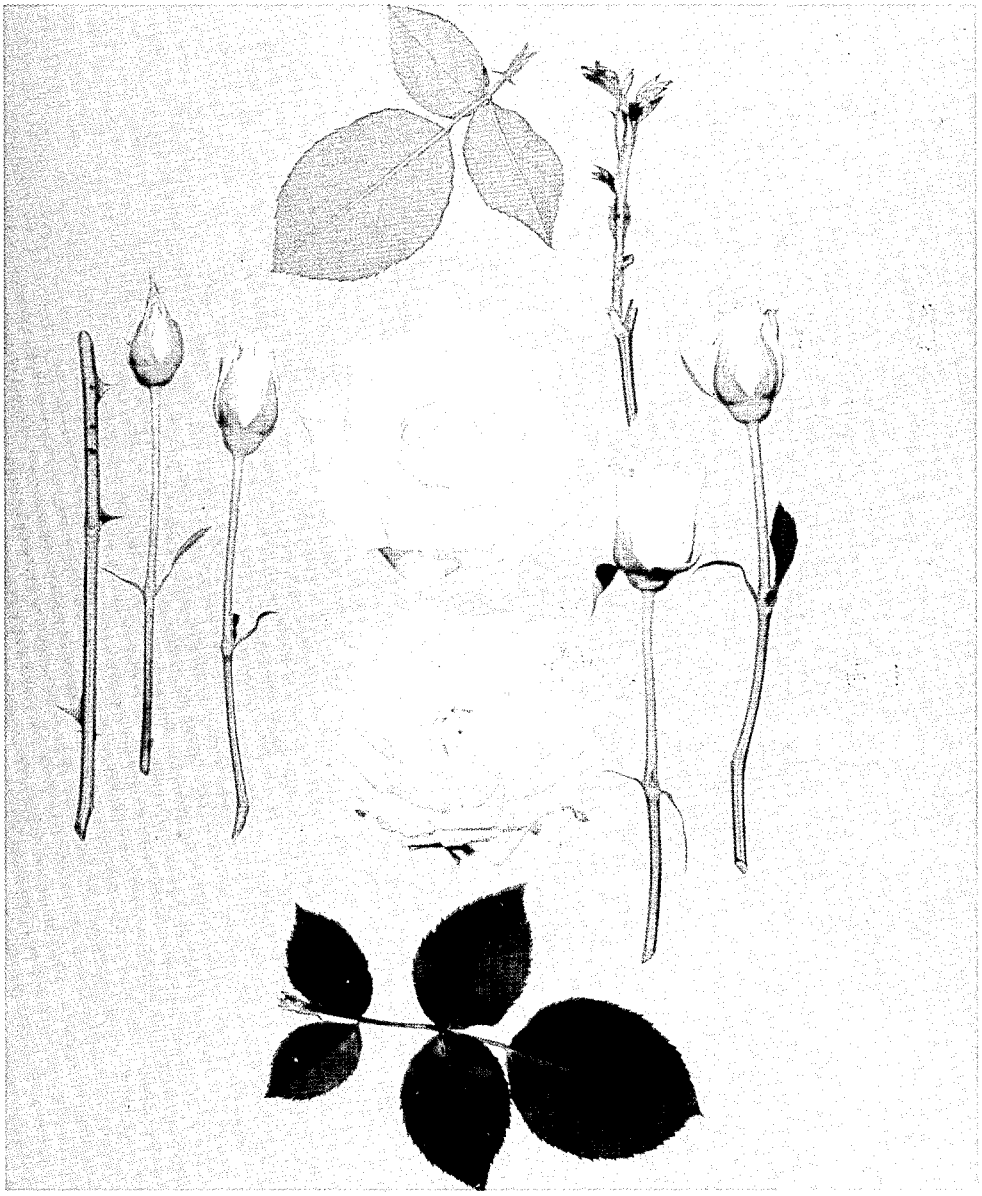

United States Patent Office

Plant Pat. 3,631
Patented Oct. 1, 1974

3,631
ROSE PLANT

Roy L. Byrum, Richmond, Ind., assignor to Joseph H. Hill Company, Richmond, Ind.

Filed Nov. 7, 1973, Ser. No. 413,638
Int. Cl. A01h *5/00*
U.S. Cl. Plt.—22 1 Claim

ABSTRACT OF THE DISCLOSURE

A new hybrid floribunda rose plant of the bi-color type suitable for greenhouse culture and distinguished by its abundant production of medium large flowers which exhibit a continuously changing coloration from bud stage to the finished bloom, the flower petals having a yellow base portion which fades to white in the upper portion and terminates in margins washed with a reddish tinge. This new rose variety is particularly distinguished by the way the flower changes color as it opens and continues to change when the bloom is fully matured, thus giving the blossom more distinctiveness both on the plant and as a cut flower.

Background of the Invention

My new variety of rose plant originated as a seedling of an unnamed yellow seedling #64–31Y × Gemini (P.P. 2,728), the crossing having been made by me in the Spring of 1968 at Richmond, Ind., with the object of developing a new yellow sweetheart variety having a larger blossom and more vigorous growth. The first flowering of this new rose plant occurred in the fall of 1969 and the unusual coloration of its blossoms caused me to select this plant for propagation with the hope that its unusual characteristics would hold true from generation to generation.

Asexual propagation of this new plant has been carried on under my direction since 1969 at Richmond, Ind., by its own rooting and at Hamilton City, Calif., by budding and the distinctive characteristics of the original seedling have been found to hold true from generation to generation and to be firmly fixed to establish this new rose plant variety.

Description of the Drawing

My new variety rose plant is illustrated by the accompanying full color photographic drawing which shows the coloring and development of the buds, the form and coloration of the newly opened and three day old blossoms, face and reverse sides of typical leaves, and specimens of new and old wood, the colors shown being as nearly true as it is reasonably possible to obtain by conventional commercial photographic procedures.

Description of the New Plant

The following is a detailed description of my new variety of rose plant, the color specifications being according to Koster's Color Guide (K) and Robert S. Wilson's Horticultural Colour Chart (W) published in London, England, by The Royal Horticultural Society. All of the following data is from observations of plants and flowers grown in greenhouses at Richmond, Indiana.

THE PLANT

Origin: Seedling (#69–37Y).
Parentage:
Seed parent—Seedling #64–31Y (unnamed).
Pollen parent—Gemini (P.P. 2,728).
Classification:
Botanical—Rosa Hybrid
Commercial—Floribunda
Form: Bush, upright and much branched.

Growth: Free and vigorous with canes of medium diameter.
Main Stems: Color—Spinach Green 0960/2 (W) some having streaks of Bistre, Plate 93 (K).
*Thorns:* Several, of medium length and downwardly hooked from a long, narrow base. Color: Van Dyck Brown, Plate 96 (K).
*Prickles and Hairs:* None.
Branches: Color—Spinach Green 0960/2 (W).
*Thorns:* Several, medium length and hooked downward from a long, narrow base. Color: Deep Carmine Violet, Plate 46 (K).
*Prickles and Hairs:* None.
New Shoots: Color—Lettuce Green, Plate 74 (K), overlaid with Erythrite Red 0027/1 ((W).
*Thorns:* Medium length, hooked downward from a long, narrow base. Color: Erythrite Red 0027 (W).
*Prickles and Hairs:* None.
*Foliage:* Quantity—abundant.
*Leaves:* Size—medium. Shape: Odd pinnate.
*Leaflets:* 5 to 7 in number. Shape: Ovoid, with acuminate apex, round base, and serrate margins. Texture: Moderately heavy. Aspect: Glossy. Color: Mature leaflets: Upper surface—Nearest color Spinach Green 0960 (W) with edges very lightly tinted with Magenta, Plate 50 (K). Under surface—Nearest color Apple Green, Plate 77 (K), some very lightly washed with Magenta, Plate 50 (K). Young leaflets: Upper surface—Spinach Green 0960/2 (W) washed or tinted with shades of Pansy Purple 928/3 (W) on the outer edges. Under surface—Lettuce Green, Plate 74 (K) tinted or washed with Erythrite Red 0027/3 (W).
*Rachis:* Medium heavy, with upper side smooth and grooved; and under side moderately prickly.
*Stipules:* Medium length and wide, with short points turning out at an angle of less than 45° and recurved toward the stem.

THE BUD

Before Calyx Breaks:
*Size:* Medium small.
*Form:* Short pointed ovoid, with a conspicuous neck and foliaceous appendages on the surface of the bud with much-cut parts extending beyond the tip of the bud and equal to one-half or more of the bud length.
*Color of Calyx:* Lettuce Green 861/3 (W).

As Calyx Breaks:
Color: Lettuce Green 861/3 (W).

As First Petal Opens:
*Size of Bud:* Medium small
*Form:* Short pointed
*Color of Petal:* Outside—Aureolin 3/2 (W). Inside—Aureolin 3/1 (W) with a very small amount of Magenta 27/2 (W) at tip of petal.

Bud Opening: Bud opens well in greenhouse.

*Sepals:* Permanent, spear-shaped, of medium length.
*Color: Inside*—Lettuce Green 861/1 (W) overlaid with white fuzz. Outside—Lettuce Green 861 (W).
*Peduncle:* Strong, erect, and of medium length and diameter.
*Bark:* Slightly rough. Color: Scheeles Green 860/1 (W).
*Prickles:* Few in number. Color: Rhodonite Red 0022/3 (W).
*Thorns and Hairs:* None.

THE FLOWER

Blooming Habit: Continuous and abundant.

Size: Medium large, 2½ to 3 inches in diameter when fully opened.

Borne: One to a stem, on strong stems of medium length.

Shape: Globular at first, becoming open. At first petals are tightly rolled outward, becoming loosely rolled outward at maturity.

Petalage: Very double with 40 to 50 petals regularly arranged.

Shape: Obovate with mucronate apex, some outside and inside petals with one notch.

Texture: Leathery and moderately thick.

Appearance: Inside—satiny; outside—shiny.

Color: All colors are from Horticultural Colour Chart (W).

(a) A newly opened greenhouse flower grown at Richmond, Indiana, and bloomed in January 1973:

*Outside Petals*

*Outer surface:* Canary Yellow 2/2 at base of petal gradually changing through 2/3 to almost white near the upper margins, the upper margins being lightly tinted with Porcelain Rose 620/3. Inside surface: Same as outside except that the upper margins are tinted with Magenta 27/2.

*Intermediate Petals*

*Outer surface:* Lemon Yellow 4/1 at base gradually changing through 4/2 to 4/3 at edge of petal.

*Inside surface:* Lemon Yellow 4/1 at base gradually changing thru 4/2 to Canary Yellow 2/3 at upper margins.

*Inner Petals*

*Outside surface:* Lemon Yellow 4/1.

*Inside surface:* Lemon Yellow 4/1.

(b) A three-day opened greenhouse grown flower in January 1973:

*Outside Petals*

*Outer surface:* Primrose Yellow 601/2 at base of petal changing through 601/3 to almost white at top of petal.

*Inside surface:* Primrose Yellow 601/2 at base of petal, changing through 601/3 to almost white at top of petal where the petal margin is tinted or washed with Magenta 27/3.

*Intermediate Petals*

*Outer surface:* Primrose Yellow 601/2 at base of petal changing through 601/3 to almost white at top of petal.

*Inside surface:* Same as outside surface except that top part of petal is tinted or washed with Magenta 27/3.

*Inner Petals*

*Outside surface:* Primrose Yellow 601/2 at base of petal changing through 601/3 to almost white at top of petal.

*Inside surface:* Same as outside of petal except that the top part of the petal is washed or tinted with Magenta 27/3.

(c) General color effect of opened flowers:

*Newly opened:* Aureolin 3/2 with various shades of Porcelain Rose 620 on some parts of the petals. This coloring changes according to the amount of sunlight that the flower receives.

*Three-day opened flower:* Aureolin 3/3 with various shades of Porcelain Rose 620 on some parts of the petals. This coloring changes according to the amount of sunlight received by the flower.

Persistence: Petals hang on and dry.

Fragrance: Slight tea.

Lasting Quality: As cut flowers—5 to 6 days at living room temperatures.

REPRODUCTIVE ORGANS

Stamens: Number—medium. Regularly arranged about pistils.

*Anthers:* Medium in size. All anthers open at once. Color: Yellow Ochre 07/2 (W).

*Filaments:* Medium in length, most have anthers. Color: Aureolin 3/1 (W).

*Pollen:* Quantity—abundant. Color: Straw Yellow 604/3 (W).

Pistils: Many in number.

*Styles:* Medium and uneven in length, moderately thin and bunched. Color: Empire Yellow 603/3 (W).

*Stigmas:* Cream Yellow, Plate 4 (K).

Ovularies: Some protruding from calyx.

Hips and Seeds: None.

This variety of rose plant is an improvement over its pollen parent Gemini (P.P. 2,728) inasmuch as it has larger blossoms, longer stems and a much more distinctive color, and is particularly distinguished by its unusual development of bi-color flower coloration from bud stage to the finished bloom. In the bud stage the flower appears to be predominately yellow with the petal edges or tips fringed with a slight reddish tinge. As the flower opens to about half-stage, the reddish tinge begins to cover more of the petal surface, thereby giving the flower more distinctiveness both on the plant and as a cut flower. The fully developed bloom then presents the soft pastel shades of pink and yellow, the yellow fading outwardly from the central portion of the flower.

The most distinctive novelty feature of this new rose plant resides in the way the flower changes color as it opens. When the flower is fully matured, it will continue to change its coloring to varying soft hues of reds, pinks and yellows.

I claim:

1. A new and distinctive variety of rose plant substantially as herein shown and described, distinguished by the unique bi-color character of its blossoms which display a continuously changing combination of reds, pinks and yellows from the first opening of the bud to the drying of the fully matured flower.

No references cited.

ROBERT E. BAGWILL, Primary Examiner